United States Patent
Salah et al.

(10) Patent No.: US 11,883,258 B2
(45) Date of Patent: Jan. 30, 2024

(54) METHOD FOR GENERATING A 3D MODEL OF A DENTAL ARCH

(71) Applicant: DENTAL MONITORING, Paris (FR)

(72) Inventors: Philippe Salah, Paris (FR); Guillaume Ghyselinck, Cantin (FR); Thomas Pellissard, Clichy (FR); Laurent Debraux, Paris (FR)

(73) Assignee: DENTAL MONITORING, Paris (FR)

(*) Notice: Subject to any disclaimer, the term of this patent is extended or adjusted under 35 U.S.C. 154(b) by 757 days.

(21) Appl. No.: 17/046,815

(22) PCT Filed: Apr. 5, 2019

(86) PCT No.: PCT/EP2019/058708
§ 371 (c)(1),
(2) Date: Oct. 12, 2020

(87) PCT Pub. No.: WO2019/197297
PCT Pub. Date: Oct. 17, 2019

(65) Prior Publication Data
US 2021/0145550 A1   May 20, 2021

(30) Foreign Application Priority Data
Apr. 13, 2018   (EP) .................. 183054558

(51) Int. Cl.
*A61C 9/00* (2006.01)
*A61B 1/24* (2006.01)
(Continued)

(52) U.S. Cl.
CPC ...... *A61C 9/0053* (2013.01); *A61B 1/000096* (2022.02); *A61B 1/00194* (2022.02);
(Continued)

(58) Field of Classification Search
CPC ..... A61C 9/0053; A61C 9/006; A61B 1/0605; A61B 1/000096; A61B 1/00194; A61B 1/24; A61B 5/0088
(Continued)

(56) References Cited

U.S. PATENT DOCUMENTS

2003/0012423 A1   1/2003   Boland et al.
2014/0365140 A1*  12/2014   Popilka ............ A61B 5/1079
                                                      702/19
(Continued)

FOREIGN PATENT DOCUMENTS

EP   1252858 A2   10/2020

OTHER PUBLICATIONS

International Search Report corresponding to International Application No. PCT/EP2019/058708 dated Jun. 6, 2019, 6 pages.
(Continued)

*Primary Examiner* — Matthew M Nelson
(74) *Attorney, Agent, or Firm* — Ronald M. Kachmarik; Cooper Legal Group LLC

(57) ABSTRACT

A method for generating a three-dimensional digital model of a dental arch of a patient. The method includes projection of at least one light beam onto the arch, so as to draw at least one light mark on the arch, and simultaneously, displacement of the arch across the beam and acquisition, during the displacement, of a series of updated images of the arch each showing an updated projection defined by the projected mark. The method includes identification of the updated projection on each updated image, then search for a three-dimensional digital model, called "updated model", exhibiting a best fit with all the updated projections.

15 Claims, 2 Drawing Sheets

(51) Int. Cl.
*A61B 1/00* (2006.01)
*A61B 1/06* (2006.01)
*A61B 5/00* (2006.01)

(52) U.S. Cl.
CPC .............. *A61B 1/0605* (2022.02); *A61B 1/24* (2013.01); *A61B 5/0088* (2013.01); *A61C 9/006* (2013.01)

(58) Field of Classification Search
USPC ........................................................ 433/213
See application file for complete search history.

(56) References Cited

U.S. PATENT DOCUMENTS

| | | | | |
|---|---|---|---|---|
| 2016/0262856 | A1* | 9/2016 | Atiya | A61B 1/253 |
| 2016/0338803 | A1* | 11/2016 | Pesach | G06T 7/74 |
| 2017/0128173 | A1 | 5/2017 | Berner et al. | |
| 2017/0215997 | A1* | 8/2017 | Martin | A61B 6/14 |
| 2017/0319057 | A1* | 11/2017 | Inglese | A61C 9/006 |
| 2018/0318051 | A1* | 11/2018 | Lu | G06V 10/44 |
| 2020/0041260 | A1* | 2/2020 | Hollenbeck | G01B 11/25 |
| 2020/0197136 | A1* | 6/2020 | Belcari | G06T 7/33 |
| 2021/0145550 | A1* | 5/2021 | Salah | A61B 5/7267 |
| 2022/0030162 | A1* | 1/2022 | Cramer | G16H 70/20 |
| 2022/0338723 | A1* | 10/2022 | Farkash | A61B 1/053 |
| 2023/0190109 | A1* | 6/2023 | Reuvenny | A61B 5/742 |
| | | | | 433/29 |
| 2023/0285124 | A1* | 9/2023 | Pesach | G06T 19/20 |
| | | | | 382/106 |

OTHER PUBLICATIONS

I. Ahmad, "Digital dental photography. Part 8: intra-oral set-ups", BDJ, vol. 207, No. 4, Aug. 22, 2009 (Aug. 22, 2009), pp. 151-157; ISSN: 0007-0610, XP055209322; entire document.

* cited by examiner

31

METHOD FOR GENERATING A 3D MODEL OF A DENTAL ARCH

TECHNICAL FIELD

The present invention relates to a method for generating a three-dimensional digital model of a dental arch of a patient, and a dental imaging device that can be implemented in the context of this method.

STATE OF THE ART

The production of orthodontic appliances relies increasingly on digital three-dimensional models of the arches of the patient. These models are conventionally obtained by means of an intra-oral optical scanner with which the orthodontist scans the arch of the patient.

This operation is costly and requires the patient to go to the orthodontist. Furthermore, an intra-oral scan is uncomfortable, even painful, and takes a long time.

US 2003/0012423 describes a method for generating a model of a tooth from images, but requires the implementation of a target, for example a rigid staple.

There is therefore a need for a novel method that makes it possible to generate a three-dimensional digital model of a dental arch of a patient and which does not have the abovementioned drawbacks.

One aim of the present invention is to at least partially address this need.

SUMMARY OF THE INVENTION

The invention relates to a method for generating a three-dimensional digital model of a dental arch of a patient, said method comprising the following steps:
A) projection of at least one light beam onto the arch, so as to draw at least one light mark on the arch;
B) simultaneously with the step A), displacement of the arch across the beam and acquisition, during said displacement, of a series of updated images of said arch each showing a representation of the projected mark or "updated projection";
C) identification of said updated projection on each updated image, then production of a three-dimensional digital model, called "updated model", exhibiting a best fit with all of the updated projections.

"Simultaneously with the step A)" is understood to mean that the series of updated images is acquired while the beam is projected. The projection can however begin before and be prolonged after the acquisition of the updated images.

A method according to the invention preferably has one or more of the following optional features:
in the step C), the updated model is sought by means of an optimization method and/or a deep learning device;
in the step C), to produce the updated model, a model defined according to the characteristics of the patient is modified;
in the step C), the updated model is determined to be the model to be tested obtained at the end of the following cycle of steps a) to c):
a) creation of a model to be tested, then
b) determination of a distance representative of the difference between all the updated projections and the model to be tested, then,
c) if said representative distance exceeds a predetermined acceptability threshold, modification of the model to be tested and return to the step a);

the representative distance is evaluated from elementary distances, each elementary distance being determined, for a respective updated projection, by an evaluation of the difference between said updated projection and an optimal reference projection,
a reference projection being a representation, on a reference image representing a view of the model to be tested, of a virtual light mark resulting from the projection, onto the model to be tested, of a virtual light beam of the same form as the light beam projected onto the arch in step A),
the optimal reference image being the reference image showing the reference projection which exhibits a minimum distance with the updated projection;
the model to be tested is segmented so as to define tooth models and the modification of the model to be tested comprises displacements of the tooth models and/or deformations of these tooth models;
the first model to be tested to be modified is a dental arch model, preferably selected according to characteristics of the patient;
in the step C), at least two methods are implemented from among the optimization methods, the artificial intelligence methods, the methods evaluating dimensions by stereovision, the methods for evaluating dimensions by analysis of the form of the light mark and the methods for evaluating dimensions by analysis of the distance between noteworthy points of the updated images;
in the step A), a structured light beam is projected;
in the step B), the patient wears a dental retractor immobilized with respect to a unit for acquiring said updated images;
in the step B), the patient displaces said arch with respect to said image acquisition unit.

The invention also proposes an acquisition device comprising:
a support;
a dental retractor fixed onto the support and defining a retractor aperture;
an updated image acquisition unit fixed to the support in a position in which it observes the retractor aperture along an optical axis.

According to a first main aspect, the device also comprises
a projector suitable for projecting a light beam toward the retractor aperture, so as to draw, when the retractor is worn by a patient, at least one light mark on an arch of the patient, said light mark being represented on each updated image by a respective updated projection, and
a processing module, preferably incorporated on this support, configured to identify the updated projections on the updated images and to produce an updated model exhibiting a best fit with all the identified updated projections.

After the retractor has been fitted onto the mouth of the patient, the image acquisition unit can thus acquire a series of updated images of the arch, each showing a representation of the mark resulting from the projection of the beam onto the arch, then produce a corresponding updated model.

The device is advantageously inexpensive, lightweight and portable, and can be implemented easily by the patient him or herself.

More generally, the device is configured to implement the step A), the acquisition of the updated images in the step B) and the step C).

According to a second main aspect, the device comprises a distance meter disposed so as to measure a distance between a point of the support, for example a point of the image acquisition unit, and an object closing the retractor aperture, for example a dental arch of the patient wearing the retractor.

The distance meter is preferably in communication with the image acquisition unit.

The processing module is preferably configured to calibrate the image acquisition unit according to a measurement received from the distance meter.

The distance meter makes it possible to accurately determine the distance between the arch and the image acquisition unit, which makes it possible to perfectly calibrate the image acquisition unit and further facilitates the search for the updated model.

A device according to the invention preferably has one or more of the following optional features:
- the beam is flat and has a thickness less than 1 mm and a width greater than 1 cm when it passes through the retractor aperture;
- the image acquisition unit and/or the processing module are incorporated on the support;
- the projector is configured to project a beam that is not visible to the naked eye;
- the projector is configured to project an ultraviolet beam;
- the image acquisition unit comprises a multispectral sensor;
- the support and/or the retractor comprise a mirror configured to reflect an image toward the image acquisition unit and/or a mirror configured to reflect the light beam, and/or a colorimetric pattern and/or a translucency pattern;
- the processing module is configured to calibrate the image acquisition unit according to an observation of the colorimetric pattern and/or of the translucency pattern;
- the support and/or the retractor comprise a thermal camera and/or a temperature probe and/or a halitus analyzer;
- the image acquisition unit is at a distance from the center of the retractor aperture less than 20 cm, even less than 10 cm;
- the projector is configured so as to vary the wavelength of the beam over time;
- the device comprises a diffuse light source;
- the light source preferably has a color rendering index greater than 80;
- the image acquisition unit is configured to control the light source.

Preferably, the method according to the invention implements an acquisition device according to the invention.

The invention relates also to:
- a computer program comprising program code instructions for implementing a step C) and, preferably, controlling the image acquisition unit and/or the projector in a step B),
- a computing medium on which such a program is stored, for example a memory or a CD-ROM, and
- an image processing module in which such a program is loaded.

Definitions

"Patient" is understood to mean any person for whom a method according to the invention can be implemented, whether or not this person is sick, or whether or not this person is undergoing treatment.

"Light mark" is understood to mean the result of the interaction between a light beam and a dental arch. A light mark can be a dot, a line, a strip or a set of dots and/or of lines and/or of strips. A line can therefore be continuous or locally interrupted and composed of pieces of lines. It can have a constant or variable width. The representation of a light mark, in particular on an updated image, varies according to the direction of observation of this mark.

The qualifier "light" includes all the electromagnetic waves from infrared to ultraviolet.

"Model" is understood to mean a three-dimensional digital representation, or "3D model".

"Image" is understood to mean a two-dimensional digital representation, such as a photograph or an image taken from a film. An image is formed by pixels.

"Image of an arch" or "model of an arch" is understood to mean a representation, in two or three dimensions, respectively, of all or part of said arch.

A reference image is an image obtained by observation of a model from a reference observation direction.

In the virtual environment of a model of an arch, a virtual beam of the same form as the beam projected onto the arch of the patient, or "updated beam", can be projected onto the model so as to obtain a so-called "virtual" light mark. The virtual light mark can be observed from different angles, each view constituting a reference image. The representation of the virtual light mark on a reference image is called "reference projection".

A historical model is an arch model from a learning base intended for training a neural network. The projection, onto a historical model, of a historical beam of the same form as the beam projected onto the arch of the patient produces a so-called "historical" light mark. The historical light mark can be observed from different angles, each view constituting a historical image. The representation of the historical light mark on a historical image is called "historical projection".

A learning base comprises historical models, preferably more than 1000, preferably more than 10 000, preferably more than 100 000 historical models, and, for each historical model, associates a set of historical projections.

A representation of the light mark on an updated image is called "updated projection".

"Match" or "fit" between two representations of an object denotes a measurement of the difference, or "distance", between these two objects. A fit is maximal ("best fit") when this difference is minimal.

Two images or "views" which exhibit a best fit ideally represent substantially one and the same object, in the same way. In other words, the representations of the object on these two images can be substantially superimposed.

An updated projection exhibits best fit with an identified reference projection on a reference image when this reference image is, from among all the reference images that can be observed on the model, that which has the reference projection separated from the updated projection by a minimum "distance". This reference projection is called "optimal".

A model exhibits best fit with a set of updated projections when a distance representative of the difference between all the updated projections and the model is minimal.

"Incorporated on the support" is understood to mean "fixed permanently onto the support".

The verbs "comprise", "include" and "have" should be interpreted in the broad and nonlimiting sense, unless indicated otherwise.

BRIEF DESCRIPTION OF THE FIGURES

Other features and advantages of the invention will become more apparent on reading the following detailed description and on studying the attached drawing in which.

DETAILED DESCRIPTION

Device

Figure 1:
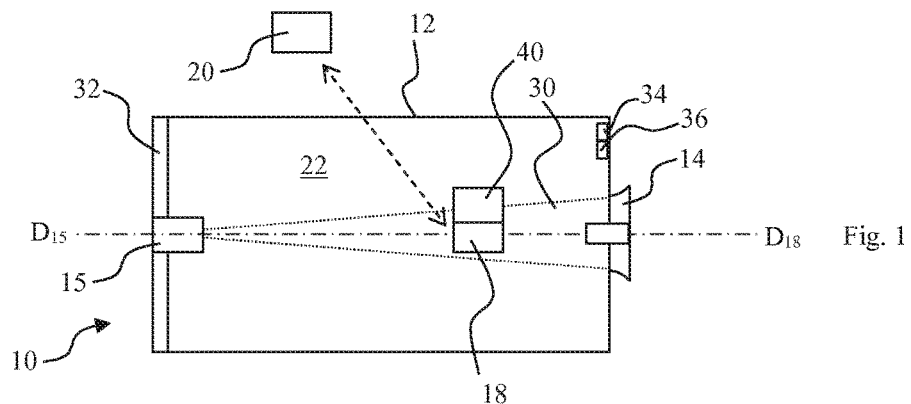
FIG. 1 schematically represents a longitudinal vertical cross section of a device according to the invention.

The acquisition device 10 represented in FIG. 1 comprises a support 12, in the form of a housing, preferably of constant length, that is to say not telescopic, onto which are fixed a dental retractor 14, a projector 15, preferably at least one mirror 16, an image acquisition unit 18, and a processing module 20, in communication with the image acquisition unit.

The support 12 defines a parallelepipedal chamber 22 of axis X, which emerges outward through a retractor aperture 24.

The support can for example be made of plastic or of cardboard.

The retractor 14 can have the characteristics of conventional retractors. It conventionally comprises a rim 26 extending around the retractor aperture and arranged so that the lips of the patient can rest thereon while revealing the teeth of the patient through said retractor aperture.

Preferably, the retractor comprises lugs for spreading the cheeks 27a and 27b in order for the image acquisition unit 18 to be able to acquire, through the retractor aperture, photos of vestibular surfaces of teeth positioned in the bottom of the mouth, such as molars. This feature is particularly advantageous for the implementation of the methods described in PCT/EP2015/074897.

The retractor 14 is preferably made of a biocompatible material, for example plastic material.

The retractor 14 can be made of a piece with the support 12 or be fixed, preferably rigidly, onto the support 12 by any means.

Preferably, the retractor is removable, that is to say that it can be mounted on and removed from the support by the patient. Advantageously, the same support can therefore be used for several retractors, and in particular for several retractors of different sizes.

The means for fixing the retractor onto the support can for example be clipping means, self-gripping strips of Velcro® type, clamping jaws, screws, magnets, or a complementarity of form between the support and the retractor.

Figure 7:
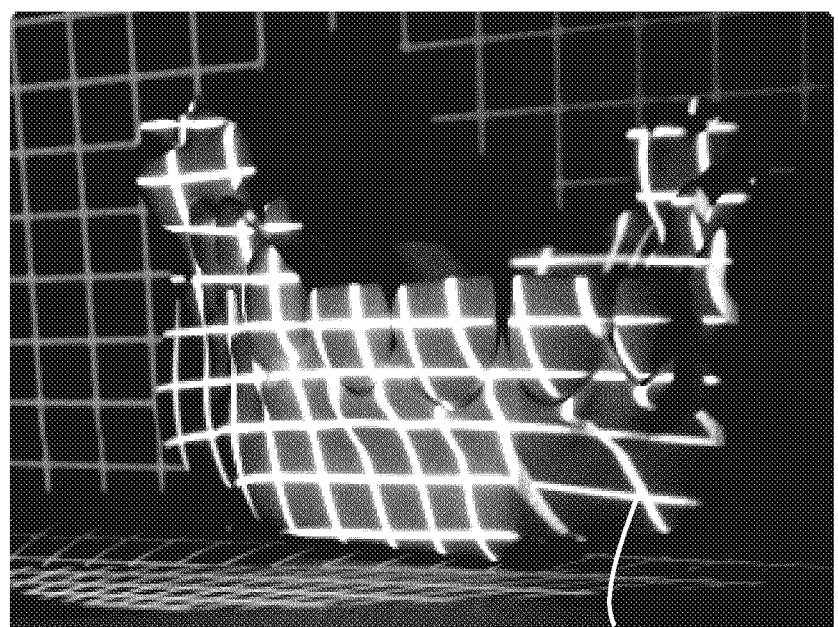
FIG. 7 represents a light mark, in this particular case a light grid, projected onto a dental arch.

The projector 15 is configured so as to project a beam 30 in the form of a light mark 31. In FIG. 7, the beam thus projects a grid which is deformed by interaction with the dental arch.

The following detailed description relates to the particular case in which the light mark is a line. The invention is not however limited to this particular case and, unless technically incompatible, the features described in the context of a line are applicable to another form of light mark.

Figure 5:
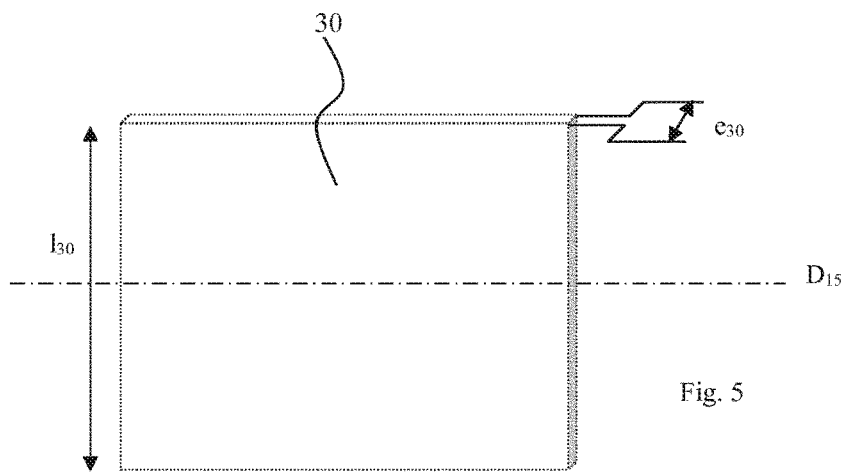
FIG. 5 schematically represents an example of beam.
Figure 6:
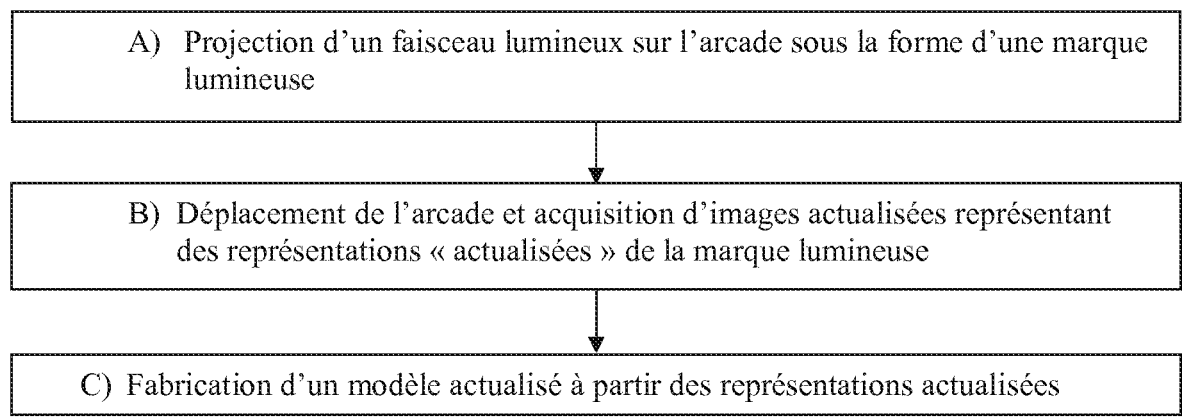
FIG. 6 schematically illustrates a method according to the invention.

When the light mark is a line, the beam has a thickness $e_{30}$ (FIG. 5), preferably constant, preferably less than 1 mm, preferably less than 0.5 mm, preferably less than 0.2 mm at its output from the projector and, preferably, when it reaches the retractor aperture.

In one embodiment, the plane of the beam forms, with the optical axis, an angle θ greater than 10°, preferably greater than 20°, 40° or 50°, and/or preferably less than 80°, preferably less than 70°. In one embodiment, the plane of the beam forms, with the optical axis, an angle θ greater than 1°, and/or preferably less than 10°, preferably less than 5°.

The projection of the beam is possible directly onto the teeth or via one or more mirrors.

The beam preferably has a width $l_{30}$ less than 1 cm, preferably greater than 2 cm when it reaches the retractor aperture.

In a cutting plane transversal to the direction of projection $D_{15}$, showing the width and the thickness of the beam, the section of the beam can have any form. Preferably, the beam is substantially flat, preferably vertical, so as to draw, on the teeth, through the retractor aperture 24, at least one deformed, possibly broken, light line.

In one embodiment, the light mark is variable in time, in particular when the beam is a structured light beam.

Preferably, the beam is a visible, infrared, ultraviolet or laser light beam, preferably not visible. The use of invisible light enhances the acceptance of the device by the patient. In particular, the patient may be stressed by a visible light, notably laser light.

An ultraviolet beam advantageously facilitates the detection of cracks in the teeth.

In one embodiment, the projector 15 is configured so as to project a beam 30 whose characteristics, and in particular the wavelength, vary over time. The analysis of the updated images is thereby enriched.

Preferably, the device comprises a light source 32, preferably diffuse, preferably composed of LEDs, suitable for projecting a light facilitating the recognition of the light mark on the images acquired, for example a light of a color complementing that of the light mark. A lighting with a blue or cyan light can be well suited to an orange light mark.

The light source preferably has a color rendering index (CRI) greater than 80, preferably greater than 90.

Preferably, the chamber 22 emerges outward only through the retractor aperture.

Preferably, the image acquisition unit is a cellphone provided with a camera. Any patient equipped with a cellphone can thus acquire updated images in the form of photos.

The image acquisition unit can be removably mounted on the support. Preferably, it is fixed non-removably, that is to say it is incorporated in the support. Advantageously, it is thus possible to permanently fix the distance between the image acquisition unit and the retractor aperture, and the angle θ between the optical axis $D_{18}$ of the image acquisition unit and the plane of the beam. The calibration of the image acquisition unit can advantageously be more accurate, which makes it possible to obtain images of optimum quality. Moreover, the fixed arrangement of the image acquisition unit and of the retractor aperture considerably facilitates the search for the updated model.

The image acquisition unit preferably supplies color images, and/or infrared images. The infrared images advantageously make it possible to show the teeth with an excellent contrast.

In one embodiment, the image acquisition unit is configured to acquire an image on demand, that is to say only when an operator triggers this acquisition.

Preferably, the image acquisition unit is configured to acquire a series comprising more than 5, 10 or 20, preferably more than 20 images per second.

Preferably, the image acquisition unit comprises a multi-spectral sensor.

The image acquisition unit is preferably at a distance $d_{18}$ from the center of the retractor aperture less than 20 cm, or 10 cm.

The mirror 16 is preferably flat. The orientation of the mirror can be fixed or variable.

The image acquisition unit is preferably fixed onto the support in a position in which it acquires a composed image comprising a direct image of the retractor aperture and an image of the retractor aperture reflected by the mirror. The mirror advantageously makes it possible to be able to observe, on one and the same composed image, the light mark from several observation directions. The direct image and the reflected image, which represent the light mark from two different observation directions, each constitute, within the meaning of the invention, an updated image.

The mirror 16 also makes it possible to acquire updated images that the image acquisition unit cannot acquire directly, for example views from above.

In the embodiment represented, the mirror 16 is fixed onto the retractor. It can also be fixed onto the support.

A mirror, identical to or different the mirror 16, can also be used to divert the light beam, in order for the updated model to be able to represent parts of the arch that are difficult, even impossible, to expose directly to the light beam.

The device can also comprise a colorimetric pattern 34 and/or a translucency pattern 36 that are fixed onto the support, preferably in the chamber 22. Advantageously, the colorimetric 34 and translucency 36 patterns make it possible, for each image, to correct the variations of hue, and facilitate the analysis of the updated image, in particular to recognize the light mark.

Preferably, the device also comprises a distance meter 40 arranged so as to measure a distance between a fixed point with respect to the support, for example a point of the image acquisition unit, and an object closing the retractor aperture.

Preferably, the device also comprises a thermal camera and/or a temperature probe and/or a halitus analyzer.

The processing module 20 can be in particular a computer incorporated on the support or software loaded into a computer, a cellphone or a tablet.

The processing module 20 preferably comprises communication means, wired or wireless, for communicating with the image acquisition unit and, if necessary, the distance meter and/or the thermal camera and/or the temperature probe and/or the halitus analyzer.

When the processing module 20 is not fixed onto the support, it preferably comprises wireless communication means, for example Bluetooth® or WiFi.

Method

The method is described in the context of a use of the acquisition device according to the invention. It is not however limited to this context.

Figure 3:
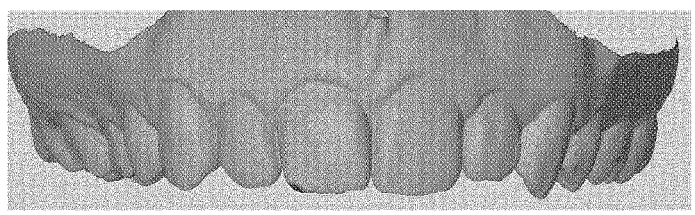
FIG. 3 represents an example of updated model.
Figure 4:
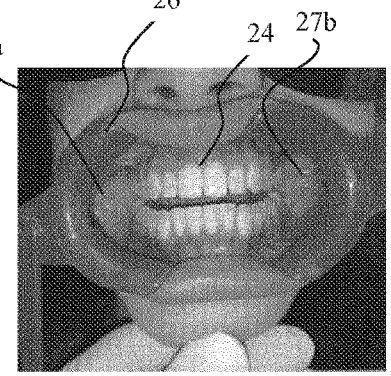
FIG. 4 represents a conventional retractor.

In the step A), the operator fixes the retractor 14 onto the support 12. The patient, who can also be the operator, then arranges his or her lips in the channels defined by the rim of the retractor. As represented in FIG. 3, the teeth of the patient are then well cleared.

By pressing the trigger on the acquisition unit, the operator provokes the emission of a light beam 30, so as to project, directly or via one or more mirrors, a light mark onto a dental arch of the patient.

In one embodiment, the beam is flat and the plane of the beam is substantially vertical when the patient holds his or her head straight.

By pressing on the trigger of the acquisition unit, the operator provokes the lighting of the light source 32 and, preferably, a calibration of the acquisition unit, preferably by using measurements performed by the distance meter. It then provokes the acquisition of a series of updated images. Preferably, this situation is retained as long as the operator maintains a pressure on the trigger.

In a preferred embodiment, the updated images are photographs or images taken from a film.

In the step B), the patient then displaces his or her teeth so that the beam travels over the arch during the acquisition of the updated images. More specifically, he or she turns his or her head with respect to the support, while keeping his or her lips on the retractor, which allows him or her to successively expose to the beam his or her incisors, canines, then molars, on one side and then on the other.

If the support comprises a mirror 16, the acquired images can be images each composed of a direct image and at least one image reflected by the mirror.

The measurements acquired by the distance meter and/or the thermal camera and/or the temperature probe and/or the halitus analyzer are transmitted to the processing module 20.

In the step C), the processing module 20 processes the acquired images, according to conventional processing methods, in order to isolate the direct image and the reflected image or images, and thus multiply the updated images.

In one embodiment, the processing comprises an operation of reversal of the reflected images and/or an operation of correction of the perspective effects and/or an operation of correction of the colors by means of the colorimetric pattern.

Then, the processing module 20 identifies the updated projections on the updated images. The identification of an updated projection on an updated image can be performed by any image processing method.

Finally, the processing module 20 searches for the updated model. The methods for this are nonlimiting.

The search for the updated model can notably result from an optimization, preferably by means of a metaheuristic method, and/or the implementation of a deep learning device.

The metaheuristic methods are known optimization methods. The method is preferably chosen from the group formed by evolutionist algorithms, preferably chosen from among:
evolution strategies, genetic algorithms, differential evolution algorithms, distribution estimation algorithms, artificial immunity systems, shuffled complex evolution path relinking, simulated annealing, and colony algorithms, particle swarm optimization algorithms, taboo search, and the GRASP method;
the kangaroo algorithm,
the Fletcher and Powell method,
the interference method,
stochastic tunneling,
random restart hill-climbing,
the cross-entropy method, and
hybrid methods between the abovementioned metaheuristic methods.

The optimization works by iteration.

Preferably, a model to be tested is created, then a distance is determined that is representative of the difference between all the updated projections and the model to be tested.

For example, if the beam is flat, the updated projection of the light mark on an updated image is formed by the representation, on that image, of the projection of a line, possibly fragmented.

If the beam is not flat, for example is made up of a grid, the updated projection of the light mark on an updated image is a complex form. FIG. 7 is an example of an updated image showing the updated projection of the grid on the arch.

To evaluate the representative distance, an elementary distance with the model to be tested is first determined for each updated representation. To this end, an optimal reference image is sought, that is to say, a view of the model to be tested which makes it possible to observe an optimal reference representation, that is to say a reference representation which most resembles the updated representation. It is then considered that the optimal reference image exhibits a best fit with the updated image.

Then, the difference between the optimal reference projection and the updated projection is evaluated, for example by calculating the average distance, in mm or in number of pixels, between these two projections. This difference can constitute the elementary distance.

The representative distance can be, for example, the average of the elementary distances. It gives an indication on the fit of the model to be tested with all the updated images of the series.

The model to be tested is then modified and the cycle resumes with the new model to be tested. The modification is preferably determined to minimize the number of cycles (evaluation of the representative distance, modification of the model to be tested).

The cycles are repeated until a representative distance is obtained that is below a predetermined acceptability threshold, preferably considered to be minimal.

The model to be tested corresponding to this representative distance constitutes the updated model.

To speed up the step C), the first model to be tested is preferably an arch model.

The first model to be tested can be a model of the arch of the patient, for example produced at the start of an orthodontic treatment. The first model to be tested can be a theoretical model, which does not represent an arch of a particular patient. Preferably, the first model to be tested is an arch model that addresses characteristics of the patient, for example an arch model that is typical of patients of the same age and/or of the same sex and/or having undergone the same treatment or a similar treatment and/or having the same number of teeth, at the same locations.

In a preferred embodiment, the model to be tested is segmented, preferably to define a tooth model for each tooth of the arch. The modification of the model to be tested can advantageously comprise displacements of the tooth models and/or deformations of these tooth models. The search for the updated model is thereby considerably accelerated.

The modifications of the successive models to be tested are determined to be realistic, for example to not lead to an interpenetration of tooth models, or to positions or deformations of teeth that are physiologically impossible.

A deep learning device, preferably a neural network, is a set of algorithms well known to the person skilled in the art.

The neural network can in particular be chosen from among:
 networks specializing in image classification, called "CNNs" ("Convolutional neural networks"), for example
  AlexNet (2012)
  ZF Net (2013)
  VGG Net (2014)
  GoogleNet (2015)
  Microsoft ResNet (2015)
  Caffe: BAIR Reference CaffeNet, BAIR AlexNet
  Torch:
  VGG_CNN_S, VGG_CNN_M, VGG_CNN_M_2048, VGG_CNN_M_1024, V GG_CNN_M_128, VGG_CNN_F, VGG ILSVRC-2014 16-layer, VGG ILSVRC-2014 18-layer, Network-in-Network (Imagenet & CIFAR-10)
  Google: Inception (V3, V4);
 networks specializing in location, and detection of objects in an image, Object Detection Networks, for example:
  R-CNN (2013)
  SSD (Single Shot MultiBox Detector: Object Detection network), Faster R-CNN (Faster Region-based Convolutional Network method: Object Detection network)
  Faster R-CNN (2015)
  SSD (2015).

The above list is not limiting.

Conventionally, the deep learning device is trained by a learning process called "deep learning".

A learning base is first of all constructed. It comprises historical arch models and, for each historical model, a set of associated historical projections.

By having, as input for the deep learning device, the historical models and the corresponding sets of historical projections, the deep learning device progressively learns to recognize, from a set of projections, patterns, and to associate them with arch models.

After having thus trained the deep learning device, the set of updated projections of the series of updated images can then be submitted to it. Thanks to its training, the deep learning device is capable of recognizing patterns therein and of determining an arch model that corresponds to this set of updated projections, and therefore that can be considered as an updated model.

Obviously, the optimization and deep learning techniques can be combined.

For example, it is possible to first use a deep learning device to create the first model to be tested, then modify this model to optimize it.

It is also possible to use a deep learning device to recognize the nature of each tooth represented on the updated images (for example "incisor" or "molar"), then search, in a tooth model base, the tooth model of the same nature which corresponds best to said tooth. The technique described above for searching for an arch model can be used to search for the tooth models.

After the tooth models have been identified, they can be arranged to form the first arch model to be tested, then modify this first model to optimize it, as described above.

Other methods for producing the updated model are also possible.

In particular, the analysis of the updated projections can allow for an evaluation of the distance between the image acquisition unit and the dental arch.

In one embodiment, the deformation of the updated projection with respect to its form is analyzed if it had been projected onto a screen at right angles to the direction of projection. This analysis makes it possible to evaluate the reliefs of the arch, that is to say the variations of distance between the projector and the arch in the region in which the light mark is projected. The algorithms that make it possible to evaluate the distance variations according to the deformation of the updated projection are known.

To remove any ambiguities, for example when the light mark extends over a region including holes, occlusions, or rapid changes of depth, the beam is preferably a structured light beam, of the type of those used by some 3D scanners, and the "Multistripe Laser Triangulation (MLT)" can in particular be used.

Still preferably, the light beam is configured to project a non-repetitive pattern onto a screen at right angles to the direction of projection, which facilitates the removal of the ambiguities.

The angle between a plane at right angles to the direction of projection $D_{15}$ of the beam and the optical axis is preferably greater than 1° and/or less than 10°, preferably less than 5°.

The analysis of the updated projections can also comprise a comparative analysis of updated projections of one and the same light mark represented on updated images taken in stereovision, that is to say taken simultaneously by several image acquisition units having different optical axes. Preferably, the angular deviation between the optical axes is greater than 1° and/or less than 10°, preferably less than 5°.

To improve the analysis of the updated projections, it is also possible to evaluate distances by analysis of the updated images. In particular, the dimensions between two noteworthy points of the retractor are known, which makes it possible to evaluate the relative displacement of the image acquisition unit with respect to the arch between two successive updated images.

The displacement of the arch across the beam can result from the displacement of the arch, the beam remaining immobile, from the displacement of the beam, the arch remaining immobile, or from the simultaneous displacement of the arch and of the beam.

In one embodiment, the displacement of the arch across the beam results exclusively from the displacement of the beam, and this displacement is controlled. The patient is then asked not to move, and the beam is displaced for it to scan the arch at a controlled speed, for example at constant speed. The controlled displacement does however necessitate the provision of means for driving the projector or a beam return mirror, for example an electric motor.

Preferably, the displacement of the arch across the beam is not mechanically controlled, notably because the patient can move his or her arches with respect to the beam at a speed which is not known.

One single method for analyzing the updated projections can therefore prove inadequate. For example, if the light mark is a vertical line and it is observed only by a single image acquisition unit, the analysis does not necessarily make it possible to determine accurate information following the direction of scrolling of the teeth across the beam.

Preferably, several analysis methods are therefore combined. Preferably, at least one of the methods implements a neutral network or a metaheuristic method.

At the end of the step C), an updated model is obtained which is a good representation of the dental arch that has been the subject of the series of updated images.

Advantageously, the method does not require the implementation of a scanner and can be implemented easily, possibly by the patient him or herself, without having to introduce any object into his or her mouth.

As now clearly emerges, a device according to the invention advantageously makes it possible to create a model of the dental arch very rapidly, without using a scanner, or an expert person, in particular a dentist or an orthodontist. The method can in particular be implemented by the patient him or herself or by someone close to him or her, anywhere, and in particular outside of a medical, dental or orthodontic practice. It does not require any particular rig to be fitted onto the arch of the patient.

Obviously, the invention is not limited to the embodiments described and represented, supplied purely for illustrative purposes.

In particular, to facilitate the analysis, the light mark can result from the projection of several lines or of a grid, or of a set of dots, preferably non-aligned, or of a strip. A light strip advantageously has a determined width, which facilitates the determination of the dimensions. Furthermore, the edges of a strip provide the same technical information as two lines. The width of the strip is preferably greater than 0.5 mm, 1 mm, 2 mm, 3 mm and/or less than 10 mm.

In one embodiment, the orientation of the beam around the direction of projection is variable. In one embodiment, it varies during the acquisition of the updated images.

Furthermore, the positions of the image acquisition unit and of the projector with respect to the plane of the retractor aperture can be different from those described above and represented. In particular, the direction of projection $D_{15}$ is not necessarily at right angles to the plane of the retractor aperture.

Figure 2:
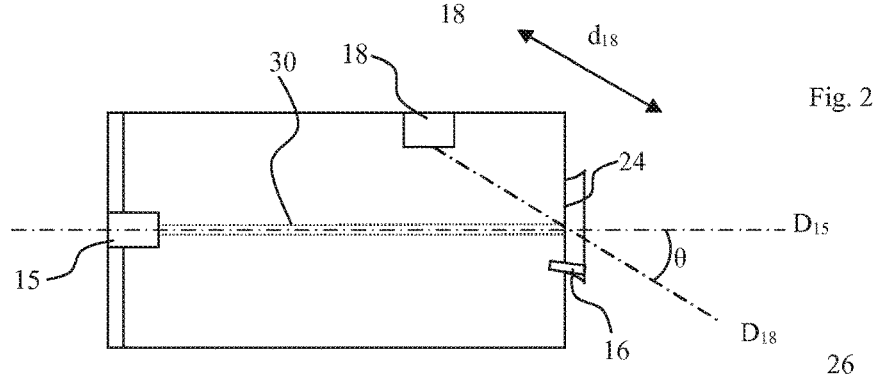
FIG. 2 represents the device of FIG. 1, seen from above.

In one embodiment, the optical axis $D_{18}$ of the image acquisition unit is at right angles to the plane of the retractor aperture. This situation corresponds, for example, to the embodiment of FIGS. 1 and 2 in which the positions of the image acquisition unit and of the projector would be reversed.

The invention claimed is:

1. A method for generating a three-dimensional digital model of a dental arch of a patient, by means of an acquisition device comprising:
    a support;
    a dental retractor fixed to the support and defining a retractor aperture;
    an updated image acquisition unit fixed to the support in a position in which it observes the retractor aperture along an optical axis;
    a projector suitable for projecting a light beam toward the retractor aperture, so as to draw, when the retractor is worn by the patient, at least one light mark on the arch of the patient, and
    a processing module,
    said method comprising the following steps:
    A) projection, by means of the projector, of at least one light beam onto the arch, so as to draw at least one light mark on the arch;
    B) simultaneously with the step A), displacement of the arch across the light beam and acquisition, during said displacement, of a series of said updated images of said arch each showing a representation of the projected light mark, or "updated projection";
    C) identification, by the processing module, of said updated projection on each updated image, then production, by the processing module, of a three-dimensional digital model, called "updated model", exhibiting a best fit with all the updated projections, the updated model being sought by means of an optimization method and/or a deep learning device.

2. The method as claimed in claim 1, wherein, in the step C), the updated model is determined to be the model to be tested obtained at the end of the following cycle of steps a) to c):
    a) creation of a model to be tested, then
    b) determination of a distance representative of the difference between all the updated projections and the model to be tested, then, c) if said representative distance exceeds a predetermined acceptability threshold, modification of the model to be tested and return to the step a), the representative distance being determined from elementary distances, each elementary distance being determined, for a respective updated projection, by an evaluation of the difference between said updated projection and an optimal reference projection, a reference projection being a representation, on a reference image representing a view of the model to be tested, of a virtual light mark resulting from the projection, on the model to be tested, of a virtual light beam of the same form as the light beam projected onto the arch in the step A), the optimal reference image being the reference image showing the reference projection which exhibits a minimum distance with the updated projection.

3. The method as claimed in claim 2, wherein the model to be tested is segmented so as to define tooth models and, in the step c), the modification of the model to be tested comprises displacements of the tooth models and/or deformations of these tooth models.

4. The method as claimed in claim 1, wherein, in the step C), to produce the updated model, a model defined according characteristics of the patient is modified.

5. The method as claimed in claim 1, wherein, in the step C), at least two methods are implemented from among the optimization methods, the artificial intelligence methods, the methods for evaluating dimensions by stereovision, the methods for evaluating dimensions by analysis of the form of the light mark and the methods for evaluating dimensions by analysis of the distance between noteworthy points of the updated images.

6. The method as claimed in claim 1, wherein, in the step A), a structured light beam is projected.

7. The method as claimed in claim 1, wherein, in the step B), the patient wears the dental retractor immobilized with respect to the unit for acquiring said updated images, and displaces said arch with respect to said image acquisition unit.

8. The method as claimed in claim 1, wherein the acquisition device comprises a mirror configured to reflect an image toward the image acquisition unit and/or a mirror configured to reflect the light beam, and/or a multispectral sensor and/or a colorimetric pattern and/or a translucency pattern and/or a thermal camera and/or a temperature probe and/or a halitus analyzer and/or a distance meter, in communication with the image acquisition unit and disposed so as to measure a distance between a point of the support and an object closing the retractor aperture.

9. The method as claimed in claim 1, wherein the updated image acquisition unit and/or the processing module are incorporated on the support.

10. The method as claimed in claim 1, wherein the projector is configured to project a beam that is not visible to the naked eye.

11. The method as claimed in claim 1, wherein the projector is configured to project an ultraviolet beam.

12. The method as claimed in claim 1, wherein the projector is configured so as to vary the wavelength and/or the form of the beam over time.

13. The method as claimed in claim 1, wherein the light mark is a dot, a line, a strip or a set of dots and/or of lines and/or of strips.

14. The method as claimed in claim 1, wherein the light mark is a line and the beam has a thickness, preferably constant, less than 1 mm at the output of the projector and when it reaches the retractor aperture.

15. The method as claimed in claim 14, wherein the plane of the beam forms, with the optical axis, an angle θ greater than 10° and less than 80°.

* * * * *